US008247009B2

(12) United States Patent
Datta et al.

(10) Patent No.: US 8,247,009 B2
(45) Date of Patent: Aug. 21, 2012

(54) BIOLOGICAL METHANE PRODUCTION FROM COAL, MANURE, SLUDGE, WASTES, OR OTHER CARBONACEOUS FEEDSTOCKS WITH SIMULTANEOUS SEQUESTRATION OF $CO_2$

(75) Inventors: Rathin Datta, Chicago, IL (US); Seth W. Snyder, Lincolnwood, IL (US); Richard D. Doctor, Lisle, IL (US); Michael P. Henry, Batavia, IL (US)

(73) Assignee: UChicago Argonne, LLC, Chicago, IL (US)

( * ) Notice: Subject to any disclaimer, the term of this patent is extended or adjusted under 35 U.S.C. 154(b) by 393 days.

(21) Appl. No.: 12/586,689

(22) Filed: Sep. 24, 2009

(65) Prior Publication Data

US 2010/0093049 A1 Apr. 15, 2010

Related U.S. Application Data

(60) Provisional application No. 61/194,755, filed on Sep. 30, 2008.

(51) Int. Cl.
*C12P 39/00* (2006.01)
*A23L 1/31* (2006.01)
(52) U.S. Cl. .......................................... 426/56; 435/42
(58) Field of Classification Search .................. 435/42; 426/56
See application file for complete search history.

(56) References Cited

U.S. PATENT DOCUMENTS

2004/0213705 A1  10/2004  Blencoe et al.

OTHER PUBLICATIONS

Borja et al., Process Biochemistry, 1913-1921, 2004.*
Schuiling et al., Enhanced Weathering: An Effective and Cheap Tool to Sequester CO2, Climatic Change (2006) 74: 349-354.
Lackner, K.S., Carbonate Chemistry for Sequestering Fossil Carbon, Annu. Rev. Energy Environ. (2002) 27: 193-232.
U.S. Department of Energy—Energy Efficiency and Renewable Energy: Energy Savers—How Anaerobic Digestion (Methane Recovery) Works (2008). http://www.energysavers.gov.
National Program 206: Manure and Byproduct Utilization, FY 2005 Annual Report, USDA Agricultural Research, http://www.ars.usda.gov.
Clean Energy Strategies for Local Governments, Landfill Methane Utilization (2008) 1-34, http://www.epa.gov/slclimat/documents.
Office of Solid Waste, Municipal Solid Waste in the United States: 2007 Facts and Figures, EPA 530-R-08-010, US EP Wash. D.C., 1-167.
U.S. Environmental Protection Agency, Identifying Opportunities for Methane Recovery at U.S. Coal Mines: Profiles of Selected Gassy Underground Coal Mines 1999-2003.
Chen et al, Economic Assessment of Biogas and Biomethane Production from Manure, CALSTART, Mar. 2010, 1-17.
J. B. Percival et al., Clay Mineralogy of Active Hydrothermal Chimneys and an Associated Mound,The Canadian Mineralogist, vol. 31 (1993), 957-971.
K.S. Lackner, Carbonate Chemistry for Sequestering Fossil Carbon, Annu. Rev. Energy Environ., 27 (2002), 193-232.
K. S. Lackner et al., Mineral Carbonates as Carbon Dioxide Sinks, LANL Internet Report LA-UR-98-4530, Los Alamos National Laboratory, (1998)1-10.
W. J. J. Huijgen et al., Carbon Dioxide Sequestration by Mineral Carbonation, Literature Review (2003), 1-52.
W.J. J. Huijgen et al., Carbon Dioxide Sequestration by Mineral Carbonation, Literature Review Update (2003-2004), 1-37.
J. Delvigne et al., Olivines, Their Pseudomorphs and Secondary Products, Pedologie XXIX, 3, (1979), 247-309.
D.S. Goldberg, Carbon Dioxide Sequestration in Deep-Sea Basalt, PNAS, vol. 105, No. 29 (2008), 9920-9925.
R. Borja et al., Response of an Anaerobic Fluidized Bed Reactor Treating Ice-cream Wastewater to Organic, Hydraulic, Temperature and pH Shocks, Journal of Biotechnology 39 (1995) 251-259.
R. Borja et al. Kinetic Study of Anaerobic Digestion of Brewery Wastewater, Process Biochemistry 29 (1994), 645-650.
J.A. Fiestas et al., Influence of Immobilization Supports on the Kinetic Constants of Anaerobic Purification of Olive Mill Wastewater, Biological Wastes 33 (1990), 131-142.
J. G. Price et al., Preliminary Assessment of the Potential for Carbon Dioxide Disposal by Sequestration in Geological Settings in Nevada, Nevada Bureau of Mines and Geology, Report 51 (2005) 1-39.
W.E. Wildman et al., Serpentine Stability in Relation to Formation of Iron-Rich Montmorillonite in Some California Soils, The American Mineralogist, vol. 56, (1971) 587-602.
H. Yang et al., The Altered Ultramafic Nodules From Mafu and Liutsu, Special Publication of the Central Geological Survey, No. 5, (1991) 39-58.
L. Neves et al., Anaerobic Co-digestion of Coffee Waste and Sewage Sludge, Waste Management 26 (2006) 176-181.
J.L. Krumhansl et al., Geochemical Implications of CO2 Sequestration in Arkosic Sandstone Reservoirs (2003), 1-13.

* cited by examiner

*Primary Examiner* — Maryam Monshipouri
(74) *Attorney, Agent, or Firm* — Olson & Cepuritis, Ltd.

(57) ABSTRACT

The present invention provides a method for generating methane from a carbonaceous fuel source with simultaneous sequestration of carbon dioxide, the method comprising anaerobically incubating a particulate alkaline earth metal salt in contact with a particulate and/or dissolved carbonaceous feedstock in a neutral or alkaline aqueous culture medium containing a culture of methanogenic bacteria consortia and collecting methane generated therefrom. At least a portion of carbon dioxide produced during the incubation reacts with the alkaline earth metal salt to form an alkaline earth metal carbonate, thereby sequestering the carbon dioxide.

21 Claims, 2 Drawing Sheets

BIOLOGICAL METHANE PRODUCTION FROM COAL, MANURE, SLUDGE, WASTES, OR OTHER CARBONACEOUS FEEDSTOCKS WITH SIMULTANEOUS SEQUESTRATION OF $CO_2$

CROSS-REFERENCE TO RELATED APPLICATIONS

This application claims the benefit of U.S. Provisional Patent Application Ser. No. 61/194,755 filed on Sep. 30, 2008, which is incorporated herein by reference in its entirety.

CONTRACTUAL ORIGIN OF THE INVENTION

The United States Government has rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

FIELD OF THE INVENTION

This invention relates to methods for producing methane. More particularly, this invention relates to methods for biological generation of methane from a carbonaceous feedstock with simultaneous sequestration of carbon dioxide.

BACKGROUND OF THE INVENTION

Methane is a fungible energy source used for power production, building heating, hot water, and cooking. Methane is also growing as a transportation fuel. Methane is one of the leading carbon feedstocks for production of chemicals and materials. In comparison to coal or petroleum, methane releases significantly smaller amounts of carbon dioxide per unit of energy produced.

Microbial conversion of carbonaceous feedstocks to methane by anaerobic bacteria is well known and used in many operations. Biogenic methane production is used in municipal waste treatment to convert sewage and activated sludge to methane to recover some of the energy and reduce the mass of waste sludge that has to be disposed. Methanogenesis is also used to treat waste from food, agricultural and chemical process industries to recover carbon and energy and reduce waste discharge loads and costs. In animal feedlots that are being increasingly used for poultry, swine and beef production, the wastes are digested to reduce discharge loads, recover some energy and reduce treatment costs. Numerous small scale digesters are used to treat human and other animal waste for the same reasons, especially in the rural areas of the less developed countries. In municipal solid waste landfills, biological methane production occurs after a period of time and now the more recent landfills are being designed and engineered to enhance biological methane production and recover energy values.

In all of these "conventional" methanogenesis applications the main carbonaceous feedstocks that are utilized are typically a mix of: 1) biopolymers, e.g., cellulose, hemicellulose, lignin, pectins, and the like; 2) fats and oils; 3) proteins; and 4) other soluble and semi-soluble organics. Based on numerous studies it is generally accepted that a consortia of anaerobic microorganisms e.g., hydrolytic acidogens, syntrophic acetogens, and methanogens, work together via highly self-regulated mechanisms to bring about this bioconversion.

Until recently, it was generally believed that fossilized carbonaceous materials such as coal, peat, petroleum, oil sands etc. could not be biomethanated as they have already undergone such bioconversion processes over a long period.

For centuries, coal and peat beds have been known to produce methane leading to numerous explosions and mining disasters. Recently however, technology development and commercialization work has begun to investigate whether methanogenesis can be enhanced and exploited to produce methane in more significant quantities, so that it can be used as a cleaner energy resource than coal with lower emissions of carbon dioxide and of other environmental pollutants such as mercury and SOx during combustion. Cultures of bacteria capable of biomethanating coal and other carbonaceous feedstocks have been identified in produced waters, manure pits, digesters, activated sludge from waste water treatment plants and as isolated cultures.

Methane, the primary component of natural gas, is perhaps the most desirable fossil fuel. It is thermodynamically stable, has very high energy content, and is readily transportable with existing pipeline infrastructure. It is currently used in almost all energy applications, even as a transportation fuel. Methane is used to produce most of the world's ammonia as well as many other chemicals. In many parts of the world such as the U.S. natural gas production has not kept up with increased demand for this fungible energy source, which has a smaller carbon footprint than other fossil fuel sources. One growing source of natural gas is coal bed methane (CBM). Regions with CBM, such as the Powder River Basin in Wyoming and Montana, have a well established infrastructure for collecting and distributing natural gas. These areas also have large coal deposits. Regions that have tar sands and oil shales also have the infrastructure for natural gas recovery.

Methanogenic bacterial consortia naturally produce methane from coal and other carbonaceous sources. The energy content of the coal is conserved in the methane. To balance the redox equation, $CO_2$ (as bicarbonate) is produced concomitantly, as described below:

$$2CH\text{ (coal)} + 2H_2O \rightarrow CH_4 \text{ (for energy)} + CO_2 \text{ (as } HCO_3^-) \tag{1a}$$

For dry, ash-free Illinois coal the formula is
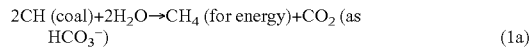
$$C_1H_{0.847}N_{0.017}O_{0.081}S_{0.017}Cl_{0.00015} \tag{1b}$$

This is a natural process that occurs in coal beds where coal bed methane (CBM) is produced, generally by the action of a consortium of anaerobic bacteria typically in a biofilm around the coal surface. An abandoned coal mine will develop a methane atmosphere over about 10 years. In the West, extraction of CBM is growing rapidly, and the U.S. Department of Energy is supporting technology development to ensure that the extraction does not cause environmental damage.

A typical methane digester converting sewage or other carbonaceous feedstocks to methane produces a gas that is typically 50 to 70% methane, with the remaining 30 to 50% being predominantly $CO_2$.

Burning of carbonaceous feedstocks releases the greenhouse gas, $CO_2$ to the atmosphere. Many developed countries either restrict these emissions or charge a fee for the amount released. Energy sources that reduce the amount of $CO_2$ release per unit of energy are increasingly desired.

From a $CO_2$ emission standpoint, the moment a carbonaceous fuel undergoes combustion, either complete or partial (such as gasification), the $CO_2$ is in a gaseous form and it can only be removed by separating it using chemical process technologies. A large amount of technical work and financial investments are being directed to improving $CO_2$ capture and sequestration performance, safety, and reliability. These techniques increase the price of energy production.

Typically, post combustion carbon capture requires handling a very large amount of material because a mole of carbon (C) produces a mole of $CO_2$, which represents a 3.7 fold increase in mass. The captured $CO_2$ gas must be compressed, put in a pipeline, and transported to a site to sequester the gas such as an oil reservoir or a deep saline aquifer. Because $CO_2$ is heavier than air, leaks in $CO_2$ pipelines are potentially co-located hazardous to human populations. Sequestration sites might be large distances from the site where $CO_2$ is captured and thus require a long and expensive pipeline. In addition, long term stability of sequestered $CO_2$ is not well understood and some losses of $CO_2$ back to the atmosphere may occur over time.

Although in situ biological methane production (e.g., in coal formations) has been investigated, the problem of carbon dioxide generation and release during biological methane production has not heretofore been addressed.

SUMMARY OF THE INVENTION

The present invention provides a method for biological methane production from a carbonaceous feedstock to generate methane, while simultaneously sequestering carbon dioxide produced during the process. The method comprises anaerobically incubating a particulate alkaline earth metal salt in contact with a particulate and/or dissolved carbonaceous feedstock in contact with a neutral or alkaline aqueous consortium of methanogenic bacteria, and collecting methane generated therefrom. The carbon dioxide generated during the incubation reacts with the particulate alkaline earth metal salt to form an alkaline earth metal carbonate (e.g., magnesium carbonate or calcium carbonate) to sequester the carbon dioxide. Preferably the mixture is incubated at a temperature in the range of about 5 to about 70° C., more preferably about 10 to 65° C., and typically about 15 to about 40° C. At least a portion of carbon dioxide produced during the incubation reacts with the alkaline earth metal salt to form an alkaline earth metal carbonate, thereby sequestering the carbon dioxide.

The alkaline earth metal salt preferably comprises an alkaline earth silicate such as magnesium silicate, calcium silicate, or a combination thereof. The alkaline earth metal salt preferably is present in the reactor in an amount in the range of about 20 to 70 percent by dry weight based on the weight of the carbonaceous feedstock. Preferably, the alkaline earth metal salt in the particulate mixture has a mean particle size in the range of about 0.01 to about 25 mm, more preferably 0.1 to about 1 mm as determined by sieve analysis. The alkaline earth salt preferably is an alkaline earth silicate, and can be a natural silicate mineral, if desired. Such natural silicate minerals can include other divalent or multivalent metal silicate species, such as iron silicates, manganese silicate, nickel silicate, and the like. For example, the natural mineral can be olivine (a magnesium and iron silicate), serpentinite (a hydrous magnesium and iron silicate), wollastonite (a calcium silicate mineral), and the like, or combinations of such mineral silicates.

The carbonaceous feedstock can be any suitable carbon-based material that can act as a nutrient source for methanogenic bacteria consortia. Preferably, the carbonaceous feedstock comprises coal, tar sand, municipal waste, agricultural residues, manure, biosolids from waste water treatment, or any combination thereof. The method of the present invention is particularly well suited for biological methane production from coal from the western United States, which contains relatively high levels of heavy metal contaminants, since the methane generated by the process is free from the heavy metal contaminants which remain in the aqueous culture, or are sequestered in the alkaline earth metal salt or produced carbonate, or both. Likewise, sulfur present in high-sulfur coal is sequestered or otherwise remains in the reactor during biomethanation of high-sulfur coal in the process of the invention. Preferably, the carbonaceous feedstock (e.g., coal) in the particulate mixture as a mean particle size in the range of about 0.01 to about 25 mm, more preferably 0.1 to about 1 mm.

The method of the present invention is performed under anaerobic conditions with an aqueous culture of methanogenic bacteria under neutral to alkaline conditions, preferably under alkaline conditions. The alkaline conditions preferably are obtained by contact of the alkaline earth metal salt with the aqueous culture medium. Preferably the aqueous culture medium includes or is in contact with nutrients such as phosphates, nitrates, ammonium ion, other carbon sources, trace minerals, or any other nutrient that may be needed for the particular biological culture being utilized, in addition to the alkaline earth metal salt and the carbonaceous feedstock. Preferred methanogenic bacterial consortia include cultures obtained from coal fields and municipal waste facilities, waste water treatment facilities, landfills, manure pits, anaerobic digesters, or isolated methanogenic cultures, which are capable of metabolizing high-carbon content to generate methane.

The methanogenesis process is performed under anaerobic conditions. Such conditions can be achieved by any method known in the art. One convenient method for achieving effective anaerobic conditions is to add an oxygen scavenging material (e.g., a reducing agent), such as sulfide ion (e.g. as $Na_2S$), to the culture medium to reduce any oxygen dissolved in the medium. Another method is to house a large volume of material in a closed reactor or vessel or an underground pit or cavern and let the biological culture consume the residual oxygen. Example of these pits are coal mines or rock quarries.

During the method of the present invention, methanogenic bacteria consortia convert carbonaceous materials into methane and carbon dioxide. At least some of the dissolved carbon dioxide produced during the process reacts with the alkaline earth metal salt to form a carbonate salt, thus stripping the carbon dioxide from the methane gas. The carbon dioxide is stripped from the gas because depleting dissolved carbon dioxide as carbonate salts causes addition carbon dioxide to dissolve in the aqueous solution to maintain equilibrium. The alkaline earth salts can also react with other acidic gaseous materials that might be produced during the biomethanation, such as sulfur oxides, hydrogen sulfide, and the like, thus affording a high quality methane product, even from carbon feedstocks, such as high-sulfur coal.

Preferably, the alkaline earth metal salts are present in the reactor in a quantity sufficient to maintain a basic pH in the culture medium and to sequester a substantial amount of the generated carbon dioxide, thus affording methane that has a carbon dioxide content of less than about 15% by weight (more preferably less than about 10 percent by weight based on the total weight of the produced gas), which has environmental benefits, by lowering the greenhouse gas content of the produced gas. The lower carbon dioxide content also decreases the subsequent purification of the biological methane required to achieve a pipeline quality natural gas. In addition, the present method has the benefit of transforming a high greenhouse gas-production capacity carbonaceous fuel such as coal, to produce a new fuel source having a lower intrinsic greenhouse gas production capacity when burned. In some embodiments of the present method the produced alkaline earth metal carbonate can be recovered and utilized for other purposes or can be left in the pit or cavern where it was formed or disposed of, if desired.

In a preferred embodiment, the mixture is incubated in a reactor, vessel, pit, or cavern with enough fluid flow to mix the carbonaceous feedstock, alkaline earth metal salt, and aqueous methanogenic bacteria culture during the incubation. The reactor should be able to achieve anaerobic conditions by either natural consumption of the residual oxygen or use of an oxygen scavenger. The reactor also preferably includes a gas collector to collect methane produced by the bacteria consortia. Optionally, the reactor can include or be connected to a scrubber for removing residual amounts of carbon dioxide or other reactive contaminant gasses (e.g., sulfides) from the produced methane.

BRIEF DESCRIPTION OF THE DRAWINGS

The invention consists of certain novel features and a combination of parts hereinafter fully described, illustrated in the accompanying drawings, and particularly pointed out in various aspects of the invention, it being understood that various changes in the details may be made without departing from the spirit, or sacrificing any of the advantages of the described invention.

DETAILED DESCRIPTION OF PREFERRED EMBODIMENTS

Figure 1:
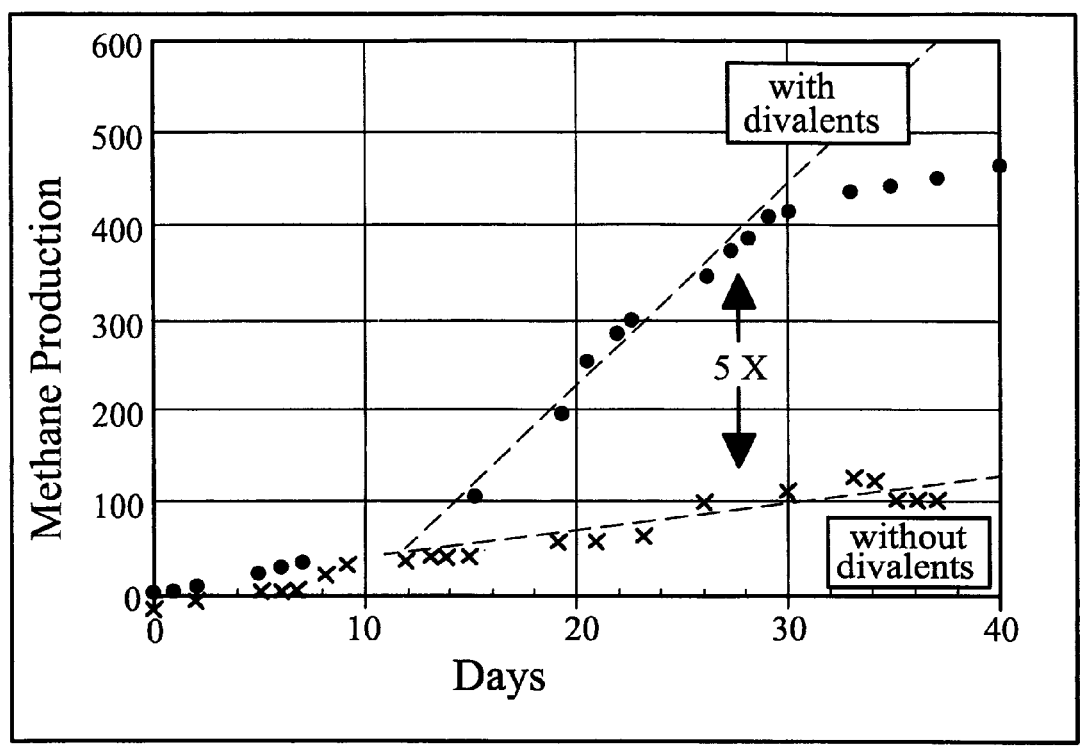
FIG. 1 includes a graph of methane generation (in milliliters) versus time (in days) for a laboratory-scale production of methane according to the present invention, compared to methane production without the presence of an alkaline earth metal salt.

The present invention biologically converts coal or other carbonaceous feedstocks or wastes, under anaerobic conditions, to methane. In the present methods, $CO_2$ produced during biomethanation is captured and sequestered by reaction with a particulate alkaline earth salt, such as Mg or Ca salts present in the culture medium. For example, ground serpentinite (magnesium silicate) or other siliceous minerals are included within the reactor in very close proximity to coal particles that are being biomethanated. The process links the biological conversion (coal being converted to methane and carbon dioxide) to a geochemical mechanism (producing solid carbonate-enriched minerals), thus sequestering the $CO_2$:

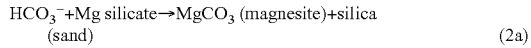
$$HCO_3^- + \text{Mg silicate} \rightarrow MgCO_3 \text{ (magnesite)} + \text{silica (sand)} \quad (2a)$$

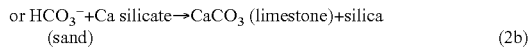
$$\text{or } HCO_3^- + \text{Ca silicate} \rightarrow CaCO_3 \text{ (limestone)} + \text{silica (sand)} \quad (2b)$$

Rapid removal of carbonate/$CO_2$ maintains a slightly basic environment, very suitable for methanogenesis. Silica is produced as a byproduct when carbon dioxide reacts with the magnesium or calcium silicate. In addition, rapid removal of carbonate (while methane evolves to the gas phase) avoids product inhibition for the biological reactions.

In nature, one major process for $CO_2$ removal from the atmosphere is direct capture by its reaction with these silicate minerals to form carbonates, as rocks weather. Along with deposition in the ocean, this is a central long-term geochemical mechanism for $CO_2$ capture and equilibration. This process is a thermodynamically favored process. In nature the atmospheric $CO_2$ concentration is low and silicate rocks have low surface area. This sequestration reaction is mediated first by $CO_2$ dissolution in surface waters, and then by carbonate contact with the rock surfaces and slow ablation of the latter. Typical half lives of natural weathering are $100^+$ to $1000^+$ years.

The methods of the present invention utilize a combination of a particulate alkaline earth metal salt with a particulate and/or dissolved carbonaceous feedstock material, so that the relatively high surface area of the feedstock improves the efficiency of the biomethanation (biological methanogenesis) process and the relatively high surface area of the particulate alkaline earth salts improves the efficiency of $CO_2$ sequestration, in comparison to biomethanylation of not particulate materials.

Coal and alkaline earth silicates or other alkaline earth salts are ground to small particle sizes (e.g. 0.1 to 1 mm) with low energy consumption and with very low cost (this is the current practice for pulverized coal fired boilers, gasifiers and mineral processing). Thus the surface areas can be greatly increased (e.g., 1000 fold or more) to vastly improve the rate of reaction of carbonate/$CO_2$ to form alkaline earth carbonates.

The pH of the methanogenic culture medium utilized in the methods of the present invention is neutral or alkaline. Preferably, the pH is in the range of about 7 to 10 (e.g., a pH of about 9).

Under anaerobic conditions, any sulfur in the coal remains reduced and SOx is not released to the atmosphere, a major environmental problem of many coals including Midwestern coal. In fact, sulfur is one of the primary limiting factors for Midwestern coal. Mercury and other heavy metals are a major environmental problem of Western coal, since these materials can be volatilized by combustion of the coal. In the methods of the present heavy metal contaminants remain with the solids in the reactor or pit and are not released to the atmosphere. In addition, the particulate nature of the carbonaceous feedstock result in significantly increased biological methane generation rates.

The following examples illustrate certain aspects of the present invention, but are not meant to be limiting.

EXAMPLE 1

The following general procedure was used for evaluating biological methane production. About 10 dry grams of ground coal (e.g., North Dakota lignite coal) and one or more alkaline earth metal salts (typically a mixture of about 10 grams of ground olivine with about 10 grams of ground serpentinite) are placed in a 1.75 inch (inner diameter) by 14 inch (length) acrylic tube containing about 240 mL of a culture medium. The tubes are sealed with top and bottom plates including ports for adding materials and slowly circulating the liquid culture medium. The aqueous culture medium preferably includes water, about 1 g/mL sodium sulfide, about 1 g/mL of dipotassium hydrogen phosphate, about 1 g/mL of ammonium chloride, along with about 2 dry grams of digested sewage sludge and about 1.1 dry grams of an activated sewage sludge from a local sewage treatment plant. Typically the sludges are added as aqueous suspension having a solids level of about 3 to 6 percent by weight. Anaerobic conditions are maintained chemically by the presence of the sodium sulfide in the medium. The ground coal and minerals typically occupy about 50 to 100 mL of the reactor tube volume, as a bed at the bottom of the tube. The culture medium is circulated through the bed of ground coal and ground minerals via a peristaltic pump connected to tubing for recirculating the culture medium through the reactor tube, the direction of flow of the culture medium being into the bottom of the reactor tube and out of the top of the reactor tube.

The medium typically is circulated at ambient room temperature (i.e., at about 21 to 23° C.), at a rate such that the entire volume of medium is completely recirculated about 1 to 5 times per week for about 1 to 6 hours per day at a rate of about 4 mL/min. The culture medium preferably is maintained at a basic pH, typically due to the presence of the ground alkaline earth silicate material. Methane produced from the bacterial action on the coal is collected in a volumetric burette so that the volume of generated gas can be determined over a period of 60 to 80 days, or until no more gas evolution is observed. For comparison, a similar experiment typically is run with ground coal in the absence of the ground alkaline earth silicates as a control. The methane production rates with and without added alkaline earth silicate are then compared. The evaluations generally are run in duplicate, and the methane production rates are averaged for the duplicate runs.

The results from experiments run under the conditions of the general procedure described above are provided in FIG. 1. In this example, each of two reactors included a ground mixture of North Dakota lignite coal obtained from the Argonne Premium Coal Facility, about 10 grams of olivine, and about 10 grams of serpentinite. The minerals were ground by breaking into 1-inch or smaller chunks with a hammer and then grinding the chunks in a mill. The coal was also ground in a mill. The particle size of both minerals and the coal were determined by dry sieving. The serpentinite, olivine and coal sieve results were as follows: 94% by weight of the serpentine had a size less than 6 mesh (about 0.13 inches or 3.4 mm); 78.6% of the olivine had a particle size of less than 6 mesh; and 98% of the coal has a sieve size of less than 20 mesh (about 0.033" or 0.85 mm). The mixture of coal and silicates was contacted with 240 mL of circulating culture medium for over 40 days at ambient room temperature as described in the general procedure. The amount of gas produced over time is provided in the graph shown in FIG. 1, compared to results from similar duplicate experiments run without the ground minerals. As shown in FIG. 1, there was an unexpected five-fold increase in methane production observed in the presence of the ground alkaline earth silicates, relative to the amount of methane produced in the absence of the silicates.

Figure 2:
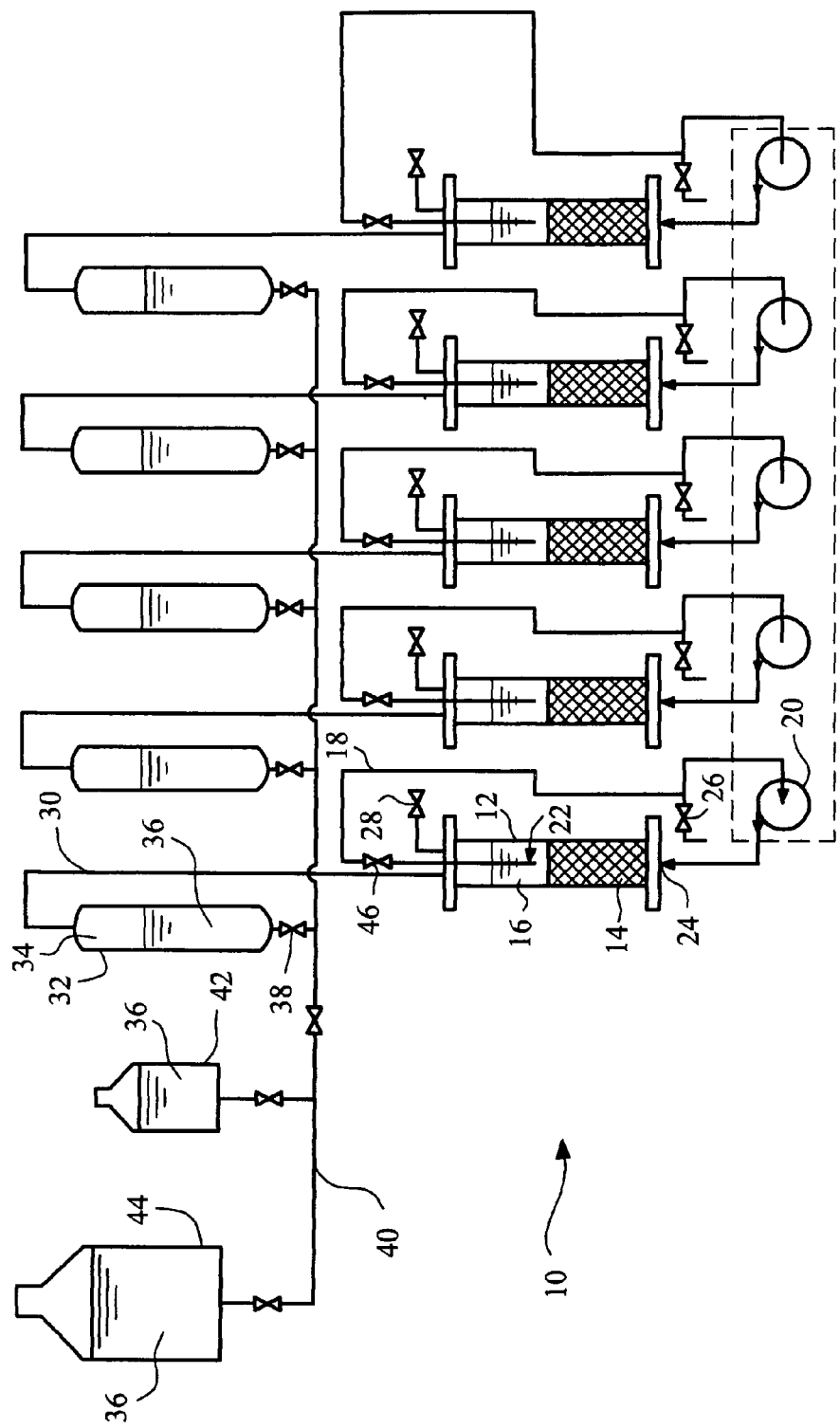
FIG. 2 depicts a bank of lab-scale reactors for producing and recovering methane according to the methods of the present invention.

The apparatus 10 utilized in the general procedure is shown schematically in FIG. 2. The apparatus 10 is composed of an array of cylindrical reactors 12, so that a number of evaluations can be performed at the same time. Each reactor 12 includes a bed of ground coal and with or without ground alkaline earth (e.g. magnesium) silicate minerals 14, in an aqueous culture medium 16. Culture medium 16 is circulated through bed 14 via a recirculating line 18 utilizing a peristaltic pump 20. Line 18 is arranged so that fluid is drawn off above bed 14 through outlet 22 and is fed back into the reactor 12 through bottom inlet 24. Line 18 also includes a sampling valve 26 for drawing a sample of the culture medium or for adding materials thereto. Each reactor 12 also includes a sample valve 28, for adding materials into the reactor or for sampling gas evolved during the process. An outlet line 30 at the top of each reactor 12 is connected to a gas collection burette 32, calibrated to measure the volume of gas 34 produced by displacement of a fluid 36 filling each burette 32. Fluid 36 preferably comprises a liquid in which carbon dioxide is insoluble, such as an acidic aqueous salt solution (e.g., 10 percent by weight aqueous sodium sulfate containing 2 percent by weight sulfuric acid). Fluid 36 is forced out of burette 32 through a valve 38 connected to a fluid leveling line 40, which in turn is connected to fluid leveling bottles 42 and 44, containing additional fluid 36. The volume of collected gas is periodically recorded so that the rate of gas production can be determined over time. Each reactor 12 also includes an inoculation sampling valve 46.

EXAMPLE 2

Additional experiments were run utilizing a mixture of about 10 grams of ground olivine and about 10 grams of ground serpentinite as the source of alkaline earth metal silicate, combined with about 10 grams of ground lignite coal under the same conditions as described in Example 1. The average number of milliliters of total gas, methane, and carbon dioxide produced per gram of dry coal/mineral feed, per day, was determined compared to similar experiments in which the ground minerals were omitted. The results are shown in Table 1.

TABLE 1

| Gas Production Data. | | | |
|---|---|---|---|
| | With olivine and serpentinite | Without minerals | Difference |
| Gas Production Rates | | | |
| mL of gas/dry g feed/day | 14.70 | 3.25 | 11.5 |
| mL of methane/dry g feed/day | 13.46 | 2.35 | 11.1 |
| mL carbon dioxide/dry g feed/day | 1.25 | 0.89 | 0.4 |
| Gas Composition | | | |
| Avg. methane % | 91.5 | 79.0 | 12.5 |
| Ave. carbon dioxide % | 8.6 | 21.0 | 40.7 |

The results in Table 1 clearly demonstrate an unexpectedly high gas production rate for the alkaline earth silicate mineral-containing example relative to the control sample without any alkaline earth silicate present (i.e., a 4.5× increase). In comparing methane production, the increase was even more dramatic (5.7×) for the mineral-containing example over the control. In addition, the ratio of methane to carbon dioxide in the collected gas was also significantly affected by the alkaline earth metal silicates, with the average percent of methane increasing to 91.5% for the mineral example relative to 79% for the control. These results demonstrate that alkaline earth salts (e.g., magnesium silicate minerals) surprisingly promote methane production, while at the same time sequestering significant amounts of the produced carbon dioxide.

EXAMPLE 3

This example demonstrates carbon dioxide capture and sequestration as metal carbonates in solid residues formed in the reactor. One important feature of this invention is that carbon dioxide is precipitated as an insoluble metal carbonate in solid residues within the reactor, effectively sequestering the carbon dioxide. Acidification by dissolved $CO_2$ solubilzes divalent or multivalent metals from the minerals present in the reactor to initiate the process. Carbonates form by reaction of minerals present in the reactor inoculum with carbon dioxide produced by anaerobic digestion of organic materials in the reactor. In this example the amount of carbon dioxide sequestered in a test reactor with minerals present was compared to the amount of carbon dioxide sequestered in a control reactor without any minerals present.

To quantitatively evaluate the production of metal carbonates, the contents of test reactor (with mineral) and control reactor (without mineral) were each separately centrifuged and washed three times with deionized water. The final centrifuge cakes were than dried at about 40° C. to constant weight to produce a dry residue, and each dry residue was then ground to about 1 mm particle size or less. Samples of the dried residues from each reactor were then acidified in a sealed bottle fitted with a gas collection device, and the gas produced upon acidification was collected and volumetrically measured. Several gas samples were analyzed and found to contain predominantly carbon dioxide (80 to 100% carbon dioxide), clearly demonstrating that carbon dioxide is sequestered as metal carbonate salts in the processes of the present invention.

The gas volume from each sample was then used to calculate the volume of carbon dioxide captured (as an insoluble carbonate) in each reactor and the volume of sequestered carbon dioxide per gram of the dry residue in each reactor. These results are tabulated in Table 2.

TABLE 2

Carbon Dioxide Captured in Test and Control Reactors

| Reactor | mL $CO_2$ from Dried Residue | mL $CO_2$ per g Dried Residue |
| --- | --- | --- |
| Control | 9.7 | 1.04 |
| Test | 29.4 | 2.10 |

The data in Table 2 show that the test reactor with added minerals had significantly more carbonate precipitate, and therefore, carbon dioxide captured, in the dried solids than the control reactor without added minerals. This example demonstrates that the addition of minerals to the biogenic methane production medium had the effect of capturing a significant fraction of the carbon dioxide that was produced during gasification of the organic substrate. These results indicate that the reduced carbon dioxide observed in the evolved gas in the test reaction (with mineral) in comparison to the control reaction (without minerals) could be attributed to precipitation of multivalent metals with carbonate.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The embodiments of the invention in which an exclusive property or privilege is claimed are defined as follows:

1. A method for generating methane from a carbonaceous feedstock with simultaneous sequestration of carbon dioxide, the method comprising anaerobically incubating a particulate alkaline earth metal salt in contact with a particulate and/or dissolved carbonaceous feedstock in a neutral or alkaline aqueous culture medium containing a culture of methanogenic bacteria consortia, and collecting methane generated therefrom; wherein at least a portion of carbon dioxide produced during the incubation reacts with the alkaline earth metal salt to form an alkaline earth metal carbonate, thereby sequestering the carbon dioxide, and the particulate alkaline earth metal salt is present in a quantity sufficient to maintain a basic pH and to sequester an amount of generated carbon dioxide such that the collected methane has a carbon dioxide content of less than about 15 percent by weight based on the weight of the methane.

2. The method of claim 1 wherein the alkaline earth metal salt comprises a magnesium silicate material.

3. The method of claim 1 wherein the alkaline earth metal salt comprises a calcium silicate material.

4. The method of claim 1 wherein the alkaline earth metal salt comprises an alkaline earth silicate optionally containing one or more additional divalent or multivalent metal silicates.

5. The method of claim 1 wherein the carbonaceous feedstock comprises coal.

6. The method of claim 5 wherein the coal is high-sulfur coal.

7. The method of claim 5 wherein the coal contains heavy metals.

8. The method of claim 1 wherein the carbonaceous feedstock comprises tar sand.

9. The method of claim 1 wherein the carbonaceous feedstock comprises municipal waste or a leachate from a municipal waste.

10. The method of claim 1 wherein the carbonaceous feedstock comprises manure, biosolids from waste water treatment, or agricultural residues.

11. The method of claim 1 wherein the alkaline earth metal salt in the particulate mixture has a mean particle size in the range of about 0.01 to about 25 mm.

12. The method of claim 1 wherein the carbonaceous feedstock in the particulate mixture has a mean particle size in the range of about 0.01 to about 25 mm.

13. The method of claim 1 wherein the aqueous culture medium has a pH in the range of about 7 to about 10.

14. The method of claim 1 wherein the culture of methanogenic bacteria comprises one or more cultures from a water from methane producing coal bed, a manure digester, a municipal waste, an activated sludge from waste water treatment, or an isolated culture of an individual methanogenic bacteria consortia.

15. The method of claim 1 wherein the collected methane has a carbon dioxide content of less than about 10 percent by weight based on the weight of the methane.

16. The method of claim 1 wherein the mixture is incubated at a temperature in the range of about 10 to about 65° C.

17. The method of claim 1 wherein the mixture is incubated in a reactor comprising a system to restrict introduction of oxygen and for maintaining an aqueous environment, and is adapted to mix the particulate carbonaceous feedstock with the particulate alkaline earth metal salt, and the methanogenic bacterial culture, and further includes a collector for collecting gaseous methane as it evolves.

18. The method of claim 1 wherein the mixture is incubated in a coal seam, a coal mine, a large hole or quarry, a seam of silicate rocks, a waste water treatment plant, an anaerobic digester, or a landfill.

19. The method of claim 1 wherein an alkaline earth carbonate is recovered in addition to methane.

20. The method of claim 18 wherein the alkaline earth carbonate is left undisturbed in the original hole, seam, or quarry where the methanogenic bacterial culture was deposited to produce methane.

21. The method of claim 1 where the alkaline earth carbonate is utilized as a long term storage for carbon dioxide.

* * * * *